United States Patent
Song et al.

(10) Patent No.: US 7,359,750 B2
(45) Date of Patent: Apr. 15, 2008

(54) APPARATUS AND METHOD FOR ANALYZING MOTIONS USING BIO-IMPEDANCE

(75) Inventors: Chul Gyu Song, #102-1007 Jungheung Apt., Seosin-dong, Wansan-gu, Jeonju-si, Jeollabuk-do 560-798 (KR); Jeong Hwan Seo, Jeonju-si (KR); Deok Won Kim, Seoul (KR); Soo Chan Kim, Seoul (KR); Dae Young Youn, Jeollabuk-do (KR); Jong Chan Kim, Seoul (KR); Hee Chang Lee, Jeonju-si (KR)

(73) Assignee: Chul Gyu Song (KR)

( * ) Notice: Subject to any disclaimer, the term of this patent is extended or adjusted under 35 U.S.C. 154(b) by 402 days.

(21) Appl. No.: 10/668,834

(22) Filed: Sep. 23, 2003

(65) Prior Publication Data

US 2004/0167420 A1  Aug. 26, 2004

(30) Foreign Application Priority Data

Feb. 22, 2003  (KR) .................. 10-2003-0011233
Sep. 5, 2003  (KR) .................. 10-2003-0062268

(51) Int. Cl.
*A61B 5/05* (2006.01)
(52) U.S. Cl. .................................... 600/547
(58) Field of Classification Search ............... 600/547, 600/595
See application file for complete search history.

(56) References Cited

U.S. PATENT DOCUMENTS 6,631,292 B1 * 10/2003 Liedtke .................. 600/547

OTHER PUBLICATIONS

Kim et al., "Evaluation of a Bio-Impedance Method for Measuring Human Arm Movement," Yonsei Medical Journal, vol. 43(5), pp. 637-645, 2002.*
Kim et al., "Human Arm Motion detection System for Robot teleoperation Using Electrical Bio-Impedance Method," 11th Inter Conf Elect Bio-Imp, Oslo, Norway, vol. 11, pp. 615-618, 2001.*

(Continued)

Primary Examiner—Max Hindenburg
Assistant Examiner—Jonathan M Foreman
(74) Attorney, Agent, or Firm—Sachman & LaPointe, P.C.

(57) ABSTRACT

Disclosed herein is an apparatus and method for measuring bio-impedance attributable to joint movement. The bio-impedance measuring apparatus includes a constant current source, current stimulus electrodes, at least two voltage detection electrodes, a demodulator, a signal gain and offset controller and an isolated amplifier. The method of measuring bio-impedance attributable to joint movement, comprising the steps: generating a weak current by use of a constant current source; causing the weak current to flow from a point to another point; forming L voltage detecting electrode pairs from voltage detecting electodes positioned at m points on each of n-1 lines that divide an interval between a first joint and a second joint, between which the weak current flows, into equal n parts (m and n are natural numbers), using combination (mC2=L); detecting bio-impedance at certain periods from J (L-K) voltage detecting electrode pairs that are obtained by subtracting K voltage detecting electrode pairs, each of which exists on a single dividing line, from the formed L voltage detecting electrode pairs; and selecting a pair of voltage detecting electrodes having a highest variation of bio-impedance.

6 Claims, 11 Drawing Sheets

OTHER PUBLICATIONS

Kim et al., "Optimal Electrode Configuration for Detection of Arm Movement using Bio-Impedance," 2nd Euro Med & Biol Eng Conf, Vienna, Austria, 2002.*

An article entitled "A New Gait Parameterization Technique By Means . . . ", By Goswami, published (1998), pp. 15-36.

Thesis entitled Development of Optical Motion Capture . . . , By JungHyun Ahn, dated Dec. 30, 1999.

* cited by examiner

extension (A) &
flexion (B) of ankle

[fig 5b]

abduction (A) &
adduction (B) of ankle

[fig 5c]

flexion (A) &
extension (B) of knee joint

[fig 5d]

supination (A) &
pronation (B) of knee joint

[fig 5e]

supination (A) & pronation (B) of hip joint

| Lower limb movement | Time interval | Movements by time |
|---|---|---|
| ankle flexion/extension 45°→110°→35° | 0~15 second : step 1 | ankle F/E |
| | 15~30 second : step 2 | knee joint F/E |
| | 30~45 second : step 3 | hip joint F/E |
| | 45~60 second : step 4 | hip joint rotation |
| | 60~75 second : step 5 | ankle F/E |
| knee joint flexion/extension 0°→−70°→0° | 0~15 second : step 1 | ankle F/E |
| | 15~30 second : step 2 | knee joint F/E |
| | 30~45 second : step 3 | hip joint F/E |
| | 45~60 second : step 4 | hip joint rotation |
| | 60~75 second : step 5 | knee joint F/E |
| hip joint flexion/extension 0°→+45°→−30° | 0~15 second : step 1 | hip joint F/E |
| | 15~30 second : step 2 | ankle F/E |
| | 30~45 second : step 3 | knee joint F/E |
| | 45~60 second : step 4 | hip joint rotation |
| | 60~75 second : step 5 | hip joint F/E |
| Heel Strike & Toe Off | 0~15 second : step 1 | HSTO |
| | 15~30 second : step 2 | knee joint F/E |
| | 30~45 second : step 3 | hip joint F/E |
| | 45~60 second : step 4 | knee joint rotation |
| | 60~75 second : step 5 | HSTO |

[fig 10]

| Lower limb movement | Interference | Definition |
|---|---|---|
| ankle flexion/extension | knee joint F/E | SNR1 |
| | hip joint F/E | SNR2 |
| | hip joint rotation (lateral/medial) | SNR3 |
| knee joint flexion/extension | ankle F/E | SNR4 |
| | hip joint F/E | SNR5 |
| | hip joint rotation (lateral/medial) | SNR6 |
| hip joint flexion/extension | knee joint F/E | SNR7 |
| | ankle F/E | SNR8 |
| | hip joint rotation (lateral/medial) | SNR9 |
| Heel Strike & Toe Off | knee joint F/E | SNR10 |
| | hip joint F/E | SNR11 |
| | knee joint rotation | SNR12 |

[fig 11]

APPARATUS AND METHOD FOR ANALYZING MOTIONS USING BIO-IMPEDANCE

BACKGROUND OF THE INVENTION

1. Field of the Invention

The present invention relates generally to an apparatus and method for analyzing motions using bio-impedance and, more particularly, to an apparatus and method for analyzing motions using the variation of bio-impedance attributable to joint movement at a certain position on a living body.

2. Description of the Related Art

Studies on the motion analysis of humans have focused on a lower limb during a gait, which employ an observational analysis method, an image analysis method, and analysis methods using an ElectroMyoGraph (EMG), a goniometer and a force plate.

The observational analysis method is disadvantageous in that accurate data cannot be obtained because measured values should be read by the human eyes.

The image analysis method obtains data necessary for gait analysis by attaching one or more reflectors to a human body, measuring the position values of the reflectors using a plurality of infrared cameras and computing the measured position values. This analysis method is capable of obtaining relatively accurate data, but disadvantageous in that the costs required to construct a system are high and the system occupies excessive space.

The EMG using bio-signals observes the states of muscles, that is, the activities of muscles, rather than direct information on the motions of a human body, so that it is unsuitable for the accurate and continuous measurements of the variations of a joint, unlike a goniometer and an image analyzer.

The goniometer is attached to a joint and analyzes the motions of the joint, so that the method using the goniometer is the most accurate analysis method. However, the goniometer is disadvantageous in that it cannot continuously measure values and restricts the free movement of joints.

The image analysis method and the method using the force plate are disadvantageous in that the sizes of the equipment therefor is large and the utilization thereof is possible only in the place where the equipment is installed. There have been utilized pressure gauges that are fabricated in the form of shoes so as to measure the pressure distribution like the force plate. However, the pressure gauges are disadvantageous in that the sizes thereof should be made to fit the feet of examinees and they should be attached to the feet of the examinees while the examinees are walking.

SUMMARY OF THE INVENTION

Accordingly, the present invention has been made keeping in mind the above problems occurring in the prior art, and an object of the present invention is to provide an apparatus for measuring bio-impedance, which does not restrict measuring space and the movement of examinees, allows measurement to be conveniently performed, and has high time resolution.

Another object of the present invention is to provide a method of measuring bio-impedance, which employs a technique of selecting the optimal positions of voltage detection electrodes with respect to each joint movement.

Another object of the present invention is to provide a system for analyzing joint movement using bio-impedance.

In order to accomplish the above object, the present invention provides an apparatus for measuring bio-impedance due to joint movement, comprising a constant current source comprised of an oscillation frequency circuit and a voltage-to-current conversion circuit for generating a weak current; current stimulus electrodes for allowing the weak current to flow from a point of a living body to another; at least two voltage detection electrodes for measuring voltage on a certain region of the living body through which the weak current flows; a demodulator for demodulating the voltage measured by the voltage detection electrodes; a signal gain and offset controller for controlling gain and offset of signals that have passed through the demodulator; and an isolated amplifier for isolating the constant current source from the signals.

In order to accomplish the above object, the present invention provides a method of measuring bio-impedance attributable to joint movement, comprising the steps generating a weak current by use of a constant current source; causing the weak current to flow from a point to another point; forming L voltage detecting electrode pairs from voltage detecting electrodes positioned at m points on each of n-1 lines that divide an interval between a first joint and a second joint, between which the weak current flows, into equal n parts (m and n are natural numbers), using combination equation ($_mC_2$=L); detecting bio-impedance at certain periods from J (L-K) voltage detecting electrode pairs that are obtained by subtracting K voltage detecting electrode pairs, each of which exists on a single dividing line, from the formed L voltage detecting electrode pairs; and selecting a pair of voltage detecting electrodes having a highest variation of bio-impedance.

In order to accomplish the above object, the present invention provides a system for analyzing joint movement using variations of bio-impedance attributable to the joint movement, comprising a constant current source comprised of an oscillation frequency circuit and a voltage-to-current conversion circuit for generating a weak current; current stimulus electrodes for allowing the weak current to flow from a point of a living body to another; a first channel comprised at least two voltage detection electrodes which positioned in a certain region between a hip joint and a knee joint, a demodulator, a gain and offset controller and an isolated amplifier; a second channel comprised at least two voltage detection electrodes which positioned in a certain region between the hip joint and an ankle joint, a demodulator, a gain and offset controller and an isolated amplifier; a third channel comprised at least two voltage detection electrodes which positioned in a certain region between a knee joint and the ankle joint, a demodulator, a gain and offset controller and an isolated amplifier; a fourth channel comprised at least two voltage detection electrodes which positioned in a certain region between the knee joint and toes, a demodulator, a gain and offset controller and an isolated amplifier; an Analog/Digital (A/D) converter for converting signals output from the channels into digital signals; and a control unit for calculating the digital signals output from the A/D converter into angular variations of the joints.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Reference now should be made to the drawings, in which the same reference numerals are used throughout the different drawings to designate the same or similar components.

Figure 1:
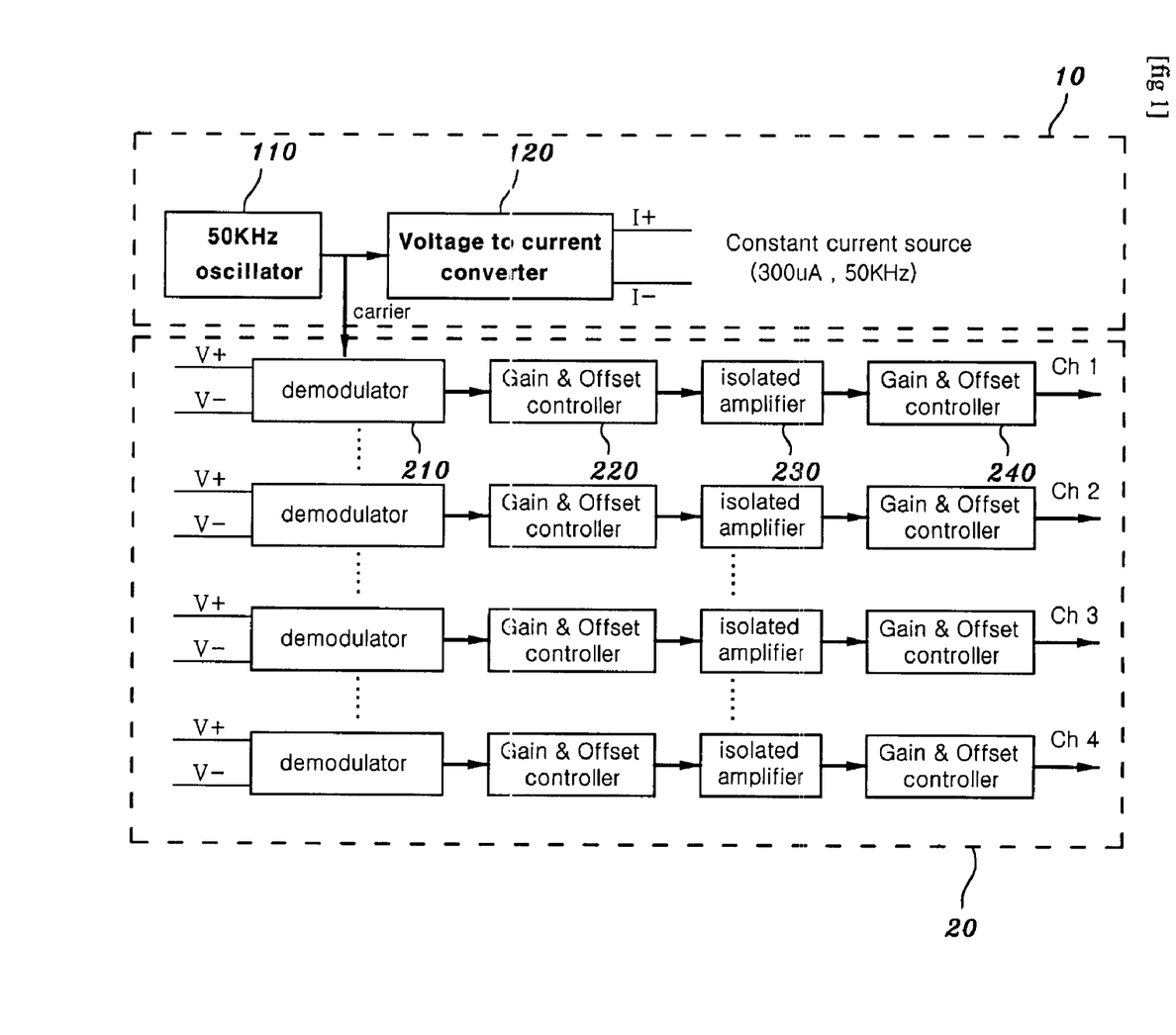
FIG. 1 is a diagram showing an apparatus for measuring bio-impedance in accordance with an embodiment of the present invention.

FIG. 1 is a diagram showing an apparatus for measuring bio-impedance in accordance with an embodiment of the present invention. Referring to this drawing, the bio-impedance measuring apparatus of the present invention is divided into a voltage detection module 10 and a current stimulus module 20 in view of the expansion of channels. A weak current is created by an oscillator 110 and a voltage-to-current converter 120.

A constant current source applies a weak current of 50 KHz, 300 μA to a lower limb through current stimulus electrodes in view of electrical safety. Bio-impedance with respect to 50 KHz has a few reactance components and many resistance components, so that the bio-impedance measuring apparatus measures only the resistance components.

When the constant current source is applied to a lower limb of a living body, a voltage can be detected by voltage detection electrodes due to the intrinsic electrical resistance component of the muscles of the lower limb. That is, there is employed a principle of detecting the variations of imped- ance attributable to the variations of the sectional areas of muscles and vessels that follow the contracting and relaxing of agonists (principal muscles) constituting the lower limb of the living body.

In a bio-impedance measuring scheme, since Nyboer applied his formula to the measurements of blood flow, Swanson's formula, which simplifies Nyboer's formula, has been widely used. In the present invention, it is assumed that factors in the variation of impedance are the variations of muscles and blood flow, unlike in the measurement of blood flow. As presented by the following Equation 1, when the distance between voltage detection electrodes is constant, voltage measured by the constant current source is directly proportional to the resistivity of muscles and vessels and a distance to a position where the voltage is measured, and reversely proportional to the sectional areas of the muscles and the vessels. Accordingly, when muscles are contracted or relaxed, bio-impedance varies due to the variations of the sectional areas of the muscles and vessels. In the following Equation 1, $Z_m$ and $Z_b$ designates the impedance of the muscles and the impedance of the vessels, respectively.

$$V = I \cdot (Z_m // Z_b) = I \cdot \left(\rho_m \frac{L}{A_m} // \rho_b \frac{L}{A_b}\right) \qquad (1)$$

V: electrical potential between voltage detection electrodes [V]

I: constant current [mA]

L: distance between voltage detection electrodes [cm]

$A_m$: sectional area of muscles between voltage detection electrodes [cm$^2$]

$\rho_m$: resistivity of muscles [Ω·cm]

$\rho_b$: resistivity of blood [Ω·cm]

Demodulators 210 demodulate signals amplitude-modu- lated by a 50 KHz oscillator 110.

If low-pass filters are added between the demodulators 210 and gain and offset controllers 220, muscle noise and motion artifacts, other than impedance signals varying according to joint movement, can be removed. Sixth order Butterworth low-pass filters are preferably used as the low-pass filters (cutoff frequency: 10 Hz).

The gain and offset controllers 220 are adapted to control impedance offset with respect to each of the channels so as to obtain a wide range of impedance variation.

Isolated amplifiers 230 isolate the constant current source from the signals using DC-DC converters (preferably PPD10-5, NEMIC-LAMBDA) and separation amplifiers (preferably ISO100, Burrbrowns) in view of the examinee's safety.

The gain and offset controllers 240 allow gain and offset to be controlled from the outside of the system.

With the above-described apparatus, bio-impedance sig- nals attributable to joint movement can be obtained.

Although four channels, that is, Ch 1, Ch 2, Ch 3 and Ch 4, have been illustrated as an example in FIG. 1, the number of channels is not limited to this. An impedance signal detected by the detection electrodes is obtained through each of the channels.

Figure 2:
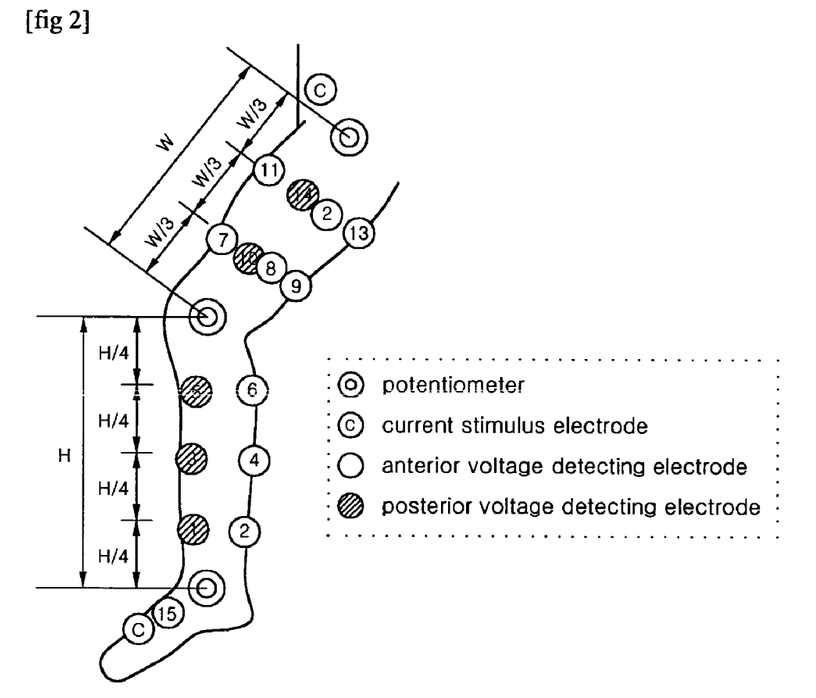
FIG. 2 is a diagram showing the arrangement of voltage detection electrodes, which is used to select the optimal positions of voltage detection electrodes so as to detect the variations of bio-impedance on a lower limb of a human body in accordance with an embodiment of the present invention.

FIG. 2 is a diagram showing the arrangement of voltage detection electrodes, which is used to select the optimal positions of voltage detection electrodes so as to detect the variations of bio-impedance on a lower limb of a human body in accordance with an embodiment of the present invention.

Referring to FIG. 2, fifteen positions to which the voltage detection electrodes are attached are selected in view of the anatomical positions of agonists, antagonists and synergists corresponding to the variations of the hip joint, the knee joint and the ankle of the lower limb. The current stimulus electrodes are attached to a lower abdominal region and a foot, respectively. The positions of the electrodes showing a best correlation between the measured values of the variation of impedance attributable to the movement of the lower limb and the measured values of the goniometer are observed. With this electrode arrangement, the variation of bio-impedance attributable to joint movement can be detected.

The portions of FIG. 2 designated by © correspond to the current stimulus electrodes that apply a constant stimulus current to the human body, while V+ and V− indicated to the left of each demodulator 21 correspond to two voltage detection electrodes. However, the number of the voltage detection electrodes is not limited to the above-described number, two. The intervals between the electrodes are set to be commonly applied to every examinee.

Since the correlation between the movements of the hip joint, the knee joint and the ankle attributable to the anatomical contraction and relaxation of muscles and the variation of impedance is not necessarily linear, a measurement method and data analysis accurately reflecting the variation of bio-impedance and the angular movement of a joint are required to evaluate the motion of a human body through the measurement of bio-impedance. The optimal positions of the electrodes satisfying these requirements are selected as shown in FIG. 2. The variation of bio-impedance is measured, with the voltage detection electrodes being attached to the leg of the lower limb so that, when the overall distance from the ankle to the knee joint is assumed to be H, the distance between two adjacent voltage detection electrodes is H/4. Additionally, the variation of impedance attributable to the variations of angles of the knee joint and the ankle is measured, with the voltage detection electrodes being attached to the thigh of the lower limb so that, when the overall distance from the knee joint to the hip joint is assumed to be W, the distance between two adjacent voltage detection electrodes is W/3. Ag—AgCl (RedDot, 3M) electrodes each having a diameter of 10 mm are employed as the electrodes. An electronic goniometer fabricated by combining a potentiometer with the goniometer is used to convert measured impedance into angles so as to obtain the angles of respective joints finally. The angles of the ankle, the knee joint and the hip joint are measured, and the values of measured impedance are corrected to angles.

The plantar flexion of the ankle is performed by gastrocnemius, while the dorsal flexion of the ankle is performed by tibialis anterior. Voltage detection electrodes 1, 2, 3, 4, 5 and 6 are used to detect the angular variations of the ankle during the flexion and extension movements of the ankle. However, the number of the voltage detection electrodes is not limited to this. Since the variation of impedance is not measured when the direction of the voltage detection electrodes is perpendicular to the direction in which current flows, the positions of the voltage detection electrodes should be properly selected. Additionally, since the variation of impedance is zero when the voltage detection electrodes are horizontally positioned, voltage detection electrode pairs each positioned horizontally are excluded from the measurement of the variations of impedance. As a result, since the number of cases with respect to the voltage detection electrodes during the movement of the ankle is the probability in which two voltage detection electrodes are selected from six voltage detection electrodes (that is, voltage detection electrodes 1, 2, 3, 4, 5 and 6), it is 6C2=15 that is calculated using combination. Since three voltage detection electrode pairs (the pairs of voltage detection electrodes 1 and 2, 3 and 4, and 5 and 6) each arranged horizontally should be excluded from the detection of the variations of bio-impedance, the possible number of cases is 12 (that is, 15–3). The variations of impedance are measured with respect to each of the twelve pairs of voltage detection electrodes 1 and 3, 1 and 4, 1 and 5, 1 and 6, 2 and 3, 2 and 4, 2 and 5, 2 and 6, 3 and 5, 3 and 6, 4 and 5, and 4 and 6 so as to ascertain the optimal positions of voltage detection electrodes for the movement of the ankle, and the positions of the pair of voltage detection electrodes having the highest variation of impedance are selected as the optimal positions.

Voltage detection electrodes 5, 6, 7, 8, 9, 10, 11, 12, 13 and 14 are used to detect the angular variations of the knee joint during the flexion and extension movements of the knee joint. However, the number of the voltage detection electrodes is not limited to this. Additionally, since the variation of impedance is zero when the voltage detection electrodes are horizontally positioned, as in the case of the movement of the ankle, voltage detection electrode pairs each positioned horizontally are excluded from the measurement of the variations of impedance. Accordingly, the pairs of voltage detection electrodes 5 and 6, 7 and 8, 7 and 9, 7 and 10, 8 and 9, 8 and 10, 9 and 10, 11 and 12, 11 and 13, 11 and 14, 12 and 13, 12 and 14, and 13 and 14 shown in FIG. 2 are excluded from the measurement of the variations of impedance. As a result, since the number of cases with respect to the voltage detection electrodes during the movement of the knee joint is the probability in which two voltage detection electrodes are selected from ten voltage detection electrodes (that is, voltage detection electrodes 5, 6, 7, 8, 9, 10, 11, 12, 13, and 14), it is 10C2=45. Since thirteen voltage detection electrode pairs each arranged horizontally should be excluded, the possible number of cases is 32 (that is, 45–13). This indicates that the optimal positions of voltage detection electrodes are ascertained through tests for thirty-two pairs of positions. The variations of impedance are measured with respect to each of the thirty two pairs of voltage detection electrodes 5 and 7, 5 and 8, 5 and 9, 5 and 10, 5 and 11, 5 and 12, 5 and 13, 5 and 14, 6 and 7, 6 and 8, 6 and 9, 6 and 10, 6 and 11, 6 and 12, 6 and 13, 6 and 14, 7 and 11, 7 and 12, 7 and 13, 7 and 14, 8 and 11, 8 and 12, 8 and 13, 8 and 14, 9 and 11, 9 and 12, 9 and 13, 9 and 14, 10 and 11, 10 and 12, 10 and 13, and 10 and 14 so as to ascertain the optimal positions of voltage detection electrodes for the movement of the knee joint, and the positions of the voltage detection electrode pair having the highest variation of impedance are selected as the optimal positions.

Eight voltage detection electrodes 7, 8, 9, 10, 11, 12, 13 and 14 are used to detect the angular variations of the knee joint during the flexion and extension movements of the hip joint. However, the number of the voltage detection electrodes is not limited to this. Additionally, since the variation of impedance is zero when the voltage detection electrodes are horizontally positioned, as in the case of the movement of the knee joint, voltage detection electrode pairs each positioned horizontally are excluded from the measurement of the variations of impedance. Accordingly, the pairs of voltage detection electrodes 7 and 8, 7 and 9, 7 and 10, 8 and 9, 8 and 10, 9 and 10, 11 and 12, 11 and 13, 11 and 14, 12 and 13, 12 and 14, and 13 and 14 shown in FIG. 2 are excluded from the measurement of the variations of impedance. As a result, since the number of cases with respect to the voltage detection electrodes during the movement of the hip joint is the probability in which two voltage detection electrodes are selected from eight voltage detection electrodes (that is, voltage detection electrodes 7, 8, 9, 10, 11, 12, 13, and 14), it is 8C2=28. Since twelve voltage detection electrode pairs each arranged horizontally should be excluded from the detection of the variations of bio-impedance, the possible number of cases is 16 (that is, 28–12). This indicates that the optimal positions of voltage detection electrodes are ascertained through tests for sixteen pairs of positions. The variations of impedance are measured with respect to each of the sixteen pairs of voltage detection electrodes 7 and 11, 7 and 12, 7 and 13, 7 and 14, 8 and 11, 8 and 12, 8 and 13, 8 and 14, 9 and 11, 9 and 12, 9 and 13, 9 and 14, 10 and 11, 10 and 12, 10 and 13, and 10 and 14 so as to ascertain the optimal positions of voltage detection electrodes for the movement of the hip joint, and the positions of the pair of voltage detection electrodes having the highest variation of impedance are selected as the optimal positions.

In order to detect heel-strike and toe-off phenomenon that occurs during a gait, a method using bio-impedance, instead of a piezoelectric sensor, is employed to detect a heel-strike and toe-off time. Five voltage detection electrodes 15, 1, 2, 3 and 4 are used to detect the heel-strike and toe-off phenomenon. However, the number of the voltage detection electrodes is not limited to this. Additionally, since the variation of impedance is zero when the voltage detection electrodes are horizontally positioned, as in the case of the movement of the knee joint, the pairs of voltage detection electrode each positioned horizontally are excluded from the measurement of the variations of impedance. Accordingly, the pairs of voltage detection electrodes 1 and 2, and 3 and 4 shown in FIG. 2 are excluded from the measurement of the variations of impedance. As a result, since the number of cases with respect to the voltage detection electrodes is the probability in which two voltage detection electrodes are selected from five voltage detection electrodes (that is, voltage detection electrodes 15, 1, 2, 3 and 4), it is 5C2=10. Since two voltage detection electrode pairs each arranged horizontally should be excluded from the detection of the variations of bio-impedance, the possible number of cases is 8 (that is, 10–2). The variations of impedance are measured with respect to each of the eight pairs of voltage detection electrodes 15 and 1, 15 and 2, 15 and 3, 15 and 4, 1 and 3, 1 and 4, 2 and 3, and 2 and 4 so as to ascertain the optimal positions of voltage detection electrodes for the heel-strike and toe-off movement, and the positions of the pair of voltage detection electrodes having the highest variation of impedance are selected as the optimal positions.

Figure 3:
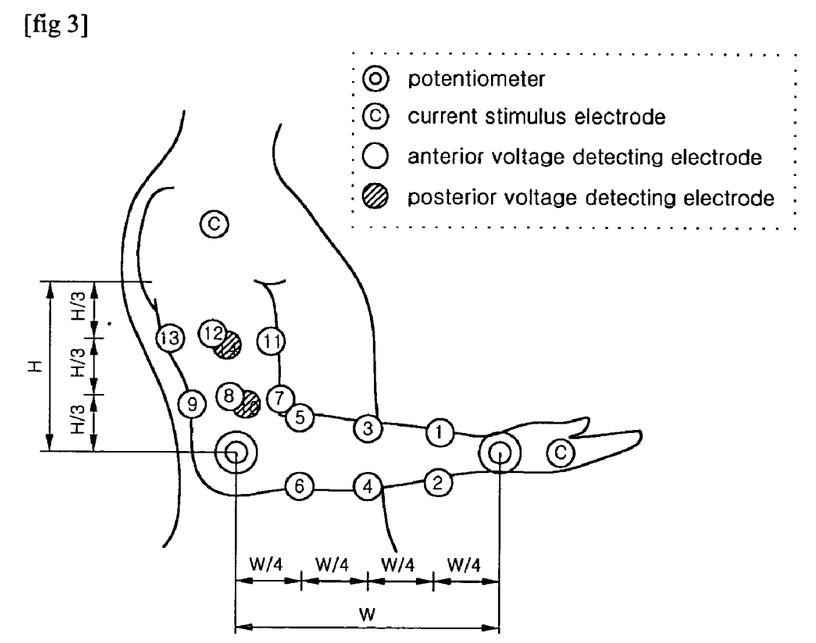
FIG. 3 is a diagram showing the arrangement of voltage detection electrodes, which is used to select the optimal positions of voltage detection electrodes so as to detect the variations of bio-impedance on an upper limb of a human body in accordance with an embodiment of the present invention.

FIG. 3 is a diagram showing the arrangement of voltage detection electrodes, which is used to select the optimal positions of voltage detection electrodes so as to detect the variations of bio-impedance on an upper limb of a human body in accordance with an embodiment of the present invention.

When in the description of FIG. 2, the ankle is replaced with a wrist, the knee joint is replaced with an elbow joint and the hip joint is replaced with a shoulder joint, the arrangement of the voltage detection electrodes, which is used to select the optimal positions of voltage detection electrodes so as to detect the variation of bio-impedance on the lower limb of the human body in the same manner. Further, the arrangement of the voltage detection electrodes, which is used to select the optimal positions of voltage detection electrodes so as to detect the variation of bio-impedance on the lower limb or the upper limb, is applied to other animals having joints in the same manner.

Figure 4:
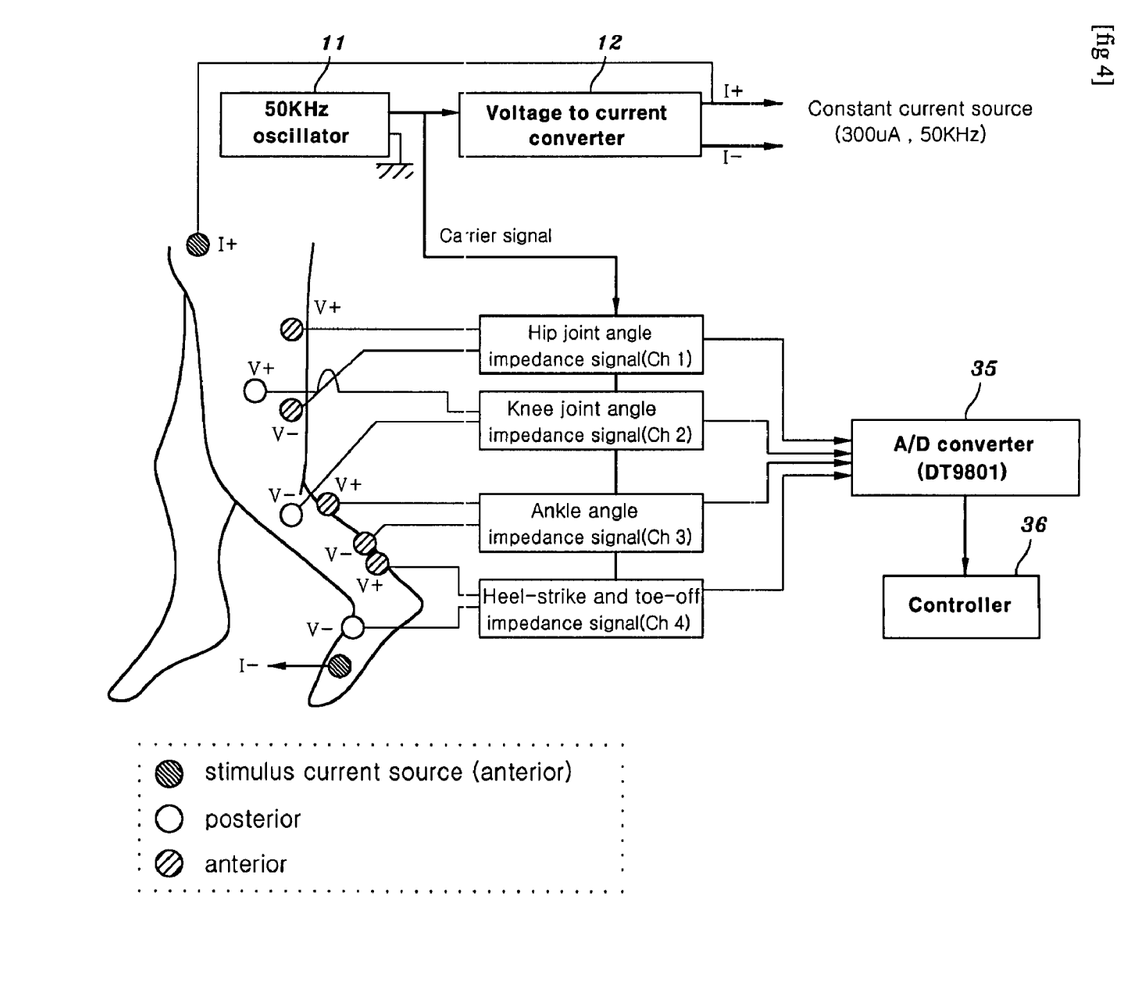
FIG. 4 is a configuration diagram showing a system for analyzing joint movement during a gait in accordance with an embodiment of the present invention.

FIG. 4 is a configuration diagram showing a system for analyzing joint movement during a gait in accordance with an embodiment of the present invention.

Referring to FIG. 4, a constant current source formed of an oscillator 11 and a voltage-to-current converter 12 applies a weak current to the lower limb with an I+ electrode attached to a thigh and an I− electrode attached to a foot so as to measure joint movement during a gait and the heel-strike and toe-off of the foot.

After the weak current is applied to measurement regions, impedance is measured using the voltage detection electrodes located at the certain positions of the human body while muscles are contracted and relaxed and, therefore, various joints are moved. The certain portions are preferably positions where the variation of impedance is largest, that is, optimal electrode positions.

The measured voltages are transmitted to an Analog/Digital (A/D) converter through channels 1, 2, 3 and 4. Said each of channels comprises a demodulator, a gain and offset controller and an isolated amplifier. Each of the channels can be extended to the A/D converter in a wired or wireless manner.

The A/D converter 35 converts the impedance signal of each channel into a digital signal. The A/D converter 35 is preferably DT9801.

The controller 36 processes the values of the flexion and extension movements of joints by processing the variations of bio-impedance attributable to the variations of the angles of joints during the gait and a bio-impedance signal attributable to the heel-strike and toe-off to obtain the variations of angles.

A process of converting resistance values obtained from bio-impedance signals into angles is described below.

Under the assumption that every human statistically has similar ranges of flexion and extension movements, the ranges of flexion and extension movements of an ankle are set to 70° and 30°, respectively, the ranges of flexion and extension movements of a knee joint are set to 0° and 90°, respectively, and the ranges of flexion and extension movements of a hip joint are set to 50° and 110°, respectively. The impedance values according to the angles of each joint can be estimated through tests. It is assumed that the values of bio-impedance obtained by maximally flexing and extending the ankle falls within a range of 1 to 30 ohm. The maximal angular ranges of the extension and flexion movements of an ankle is 70 to 0 degrees and 0 to 30 degrees, that is, 70 degrees+30 degrees=100 degrees. Accordingly, 1 ohm corresponds to 70 degrees for the extension movement, and 30 ohms corresponds to 30 degrees for the flexion movement. (Angle)/(bio-impedance value) is 100 degrees/30 ohm=3.333 degrees/1 ohm. Accordingly, the angular values of the flexion and extension movements can be calculated based on the variation of bio-impedance by calculating the angular values in such a way as to vary each of the angular values by 3.3333 degrees as the bio-impedance varies by 1 ohm.

For the knee joint and the hip joint, in the case of heel-strike and toe-off, the angular values of flexion and extension thereof can be calculated by the above-described method. Furthermore, for a living body having joints, the angular values of the joints can be calculated using impedance signals by the above-described method.

Figure 5A:
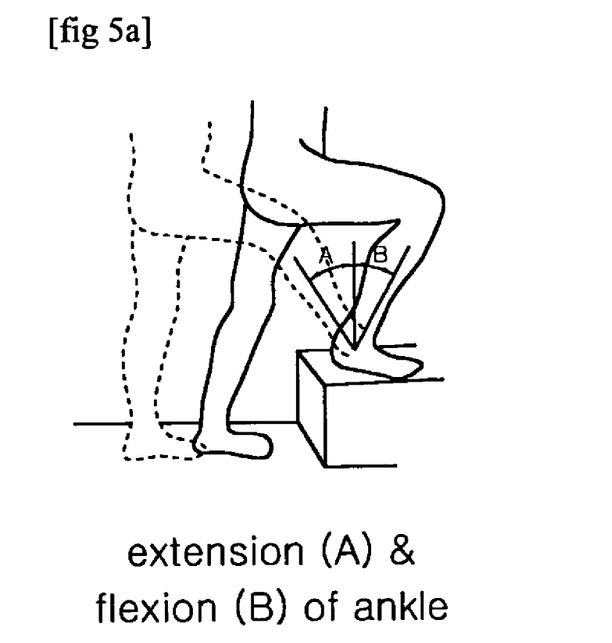
FIGS. 5a to 5e are diagrams showing examples of the movements of the lower limb.
Figure 5B:
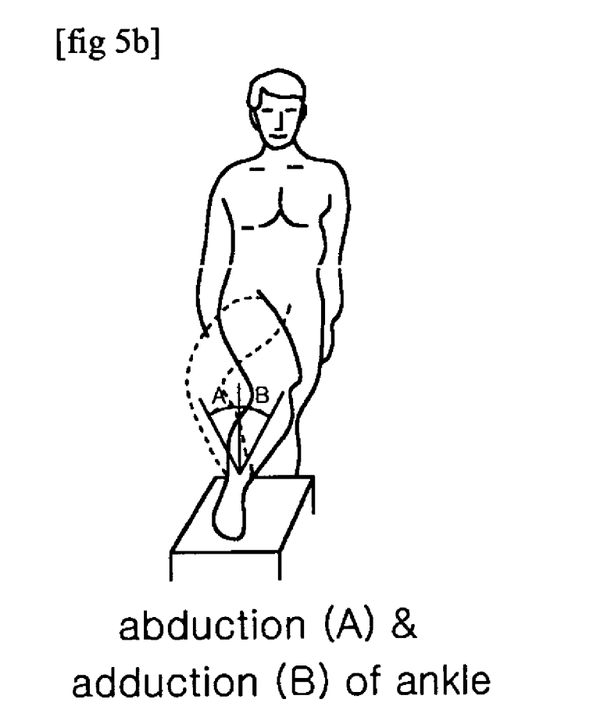
Figure 5C:
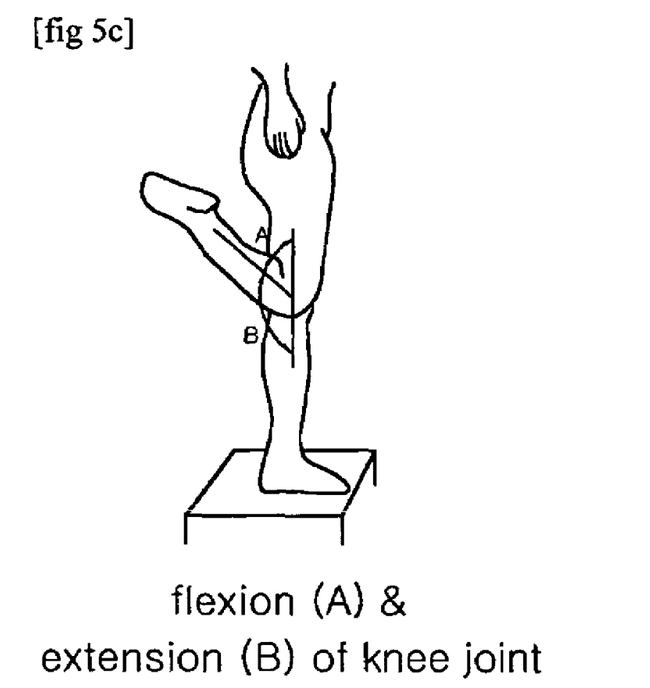
Figure 5D:
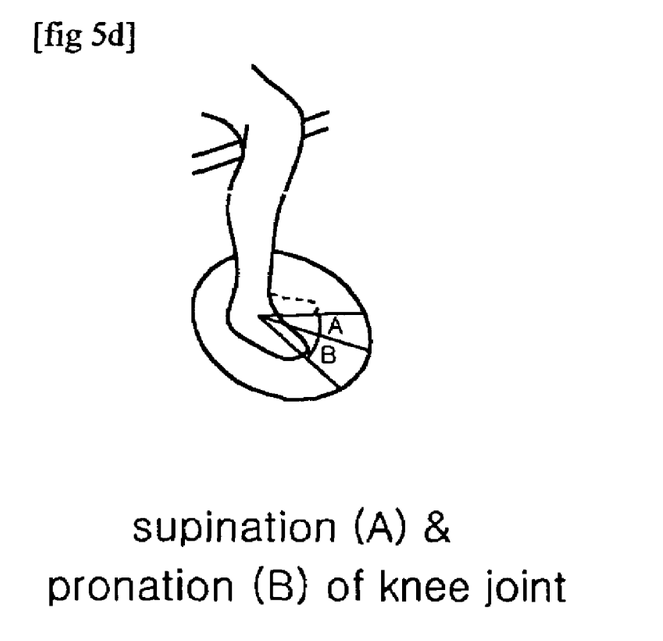
Figure 5E:
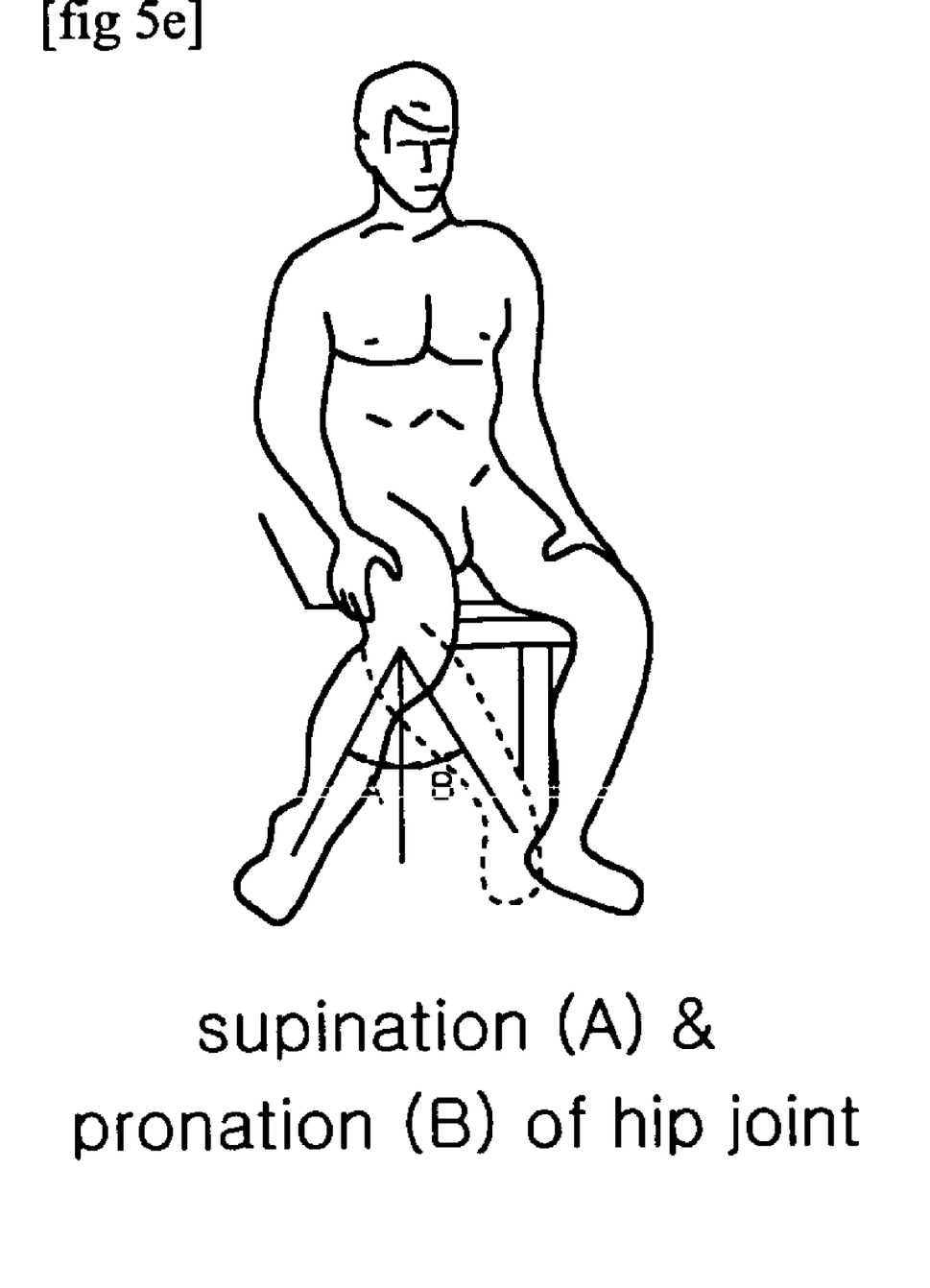
Figure 6:
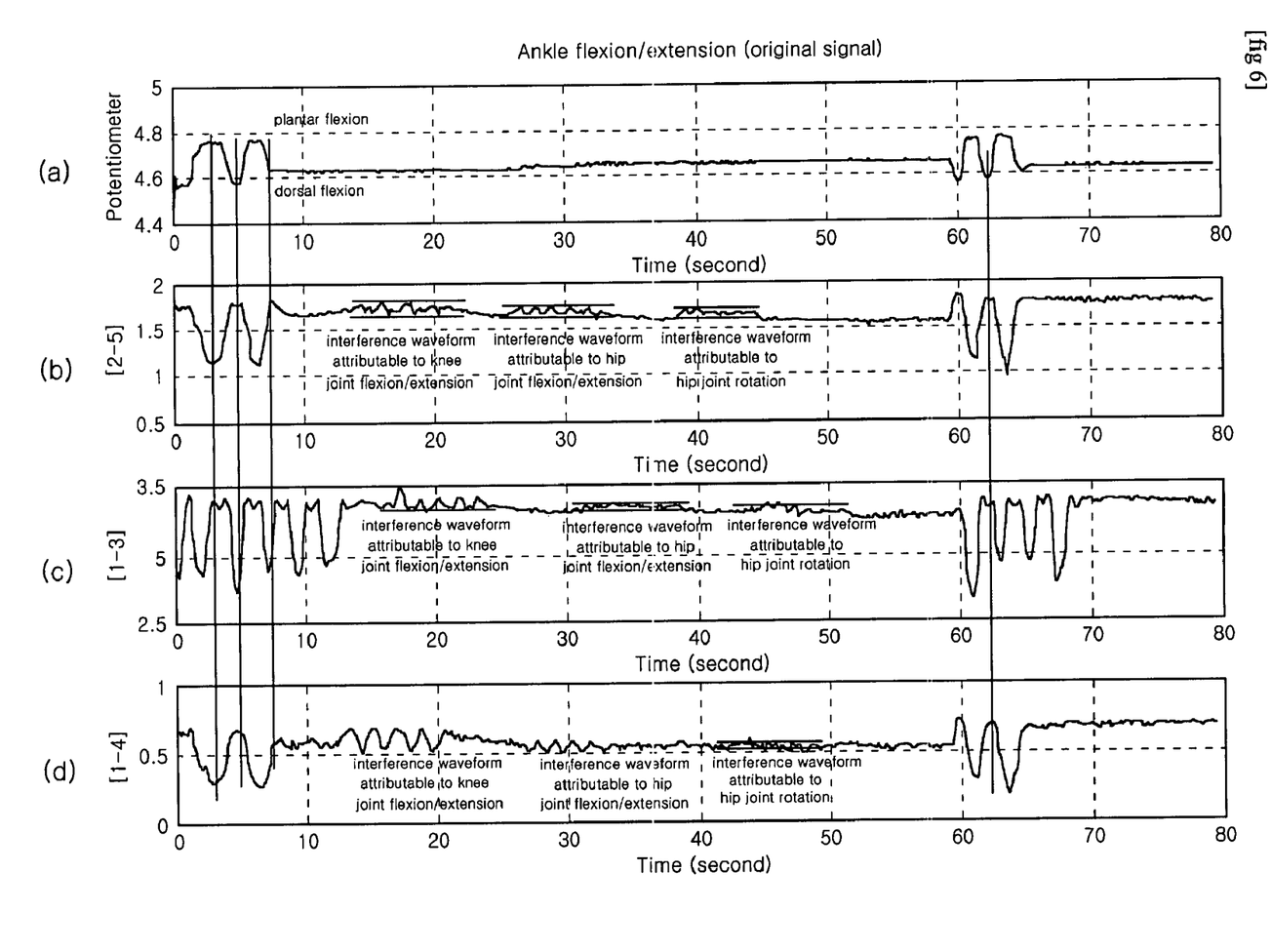
FIGS. 6a to 6d are graphs that are presented to compare a signal measured by the electronic goniometer with signals measured by the voltage detection electrodes with respect to the detection of the angles of ankle movement.

FIGS. 5*a* to 5*e* are diagrams showing examples of the movements of a lower limb, that is, examples of the joint movements of the lower limb, in which FIG. 5a shows the extension A and flexion B of an ankle, FIG. 5b shows the abduction A and adduction B of the ankle, FIG. 6c shows the flexion A and extension B of a knee joint, FIG. 6d shows the supination A and pronation B of the knee joint, and FIG. 6e shows the supination A and pronation B of a hip joint.

FIGS. 6a to 6d are graphs that are presented to compare a signal measured by the electronic goniometer with signals measured by the voltage detection electrodes with respect to the detection of the angles of ankle movement.

FIGS. 6a to 6d show the variations of angles during the flexion and extension movements of an ankle, in which FIG. 6a shows values measured by the electronic goniometer, FIG. 6b shows values measured by the pair of voltage detection electrodes 2 and 5, FIG. 6c shows values measured by the pair of voltage detection electrodes 1 and 3, and FIG. 6d shows values measured by the pair of voltage detection electrodes 1 and 4.

The present invention allows the angular variation of a joint to be measured without using the electronic goniometer. Accordingly, the angular values of the vertical axis of FIG. 6 can be obtained by attaching an electronic goniometer electrode and bio-voltage detection electrode pair to the region of the ankle, simultaneously measuring the voltage variation of the electronic goniometer and the variation of the bio-impedance due to the angular variation of the joint and converting the variation of the bio-impedance into angular values.

The positions of electrode signals having the lowest influence of interference as a result of an analysis of the influence of interference due to joint movement other than ankle movement and the highest correlation with the signals of the goniometer is selected as optimal electrode positions. It can be appreciated that electrode positions having the highest correlation coefficient with the angular variation of the flexion and extension movements of the ankle measured by the electronic goniometer are the positions of the electrodes 2 and 5. In this case, the highest correlation coefficient is −0.913. The correlation coefficient can be obtained by simultaneously obtaining the signals of the goniometer and bio-impedance due to joint movement while flexing and extending an ankle for 10 seconds and obtaining Pierson's correlation coefficient and the coefficients of a polynomial expression.

The reason why the measured values of the electronic goniometer and the bio-impedance are compared with each other is to show that the angular variation of the joint can be conveniently measured using only bio-impedance.

FIGS. 7a to 7d are graphs that are presented to compare a signal measured by the electronic goniometer with signals measured by the voltage detection electrodes with respect to the detection of the angles of knee joint movement.

Figure 7:
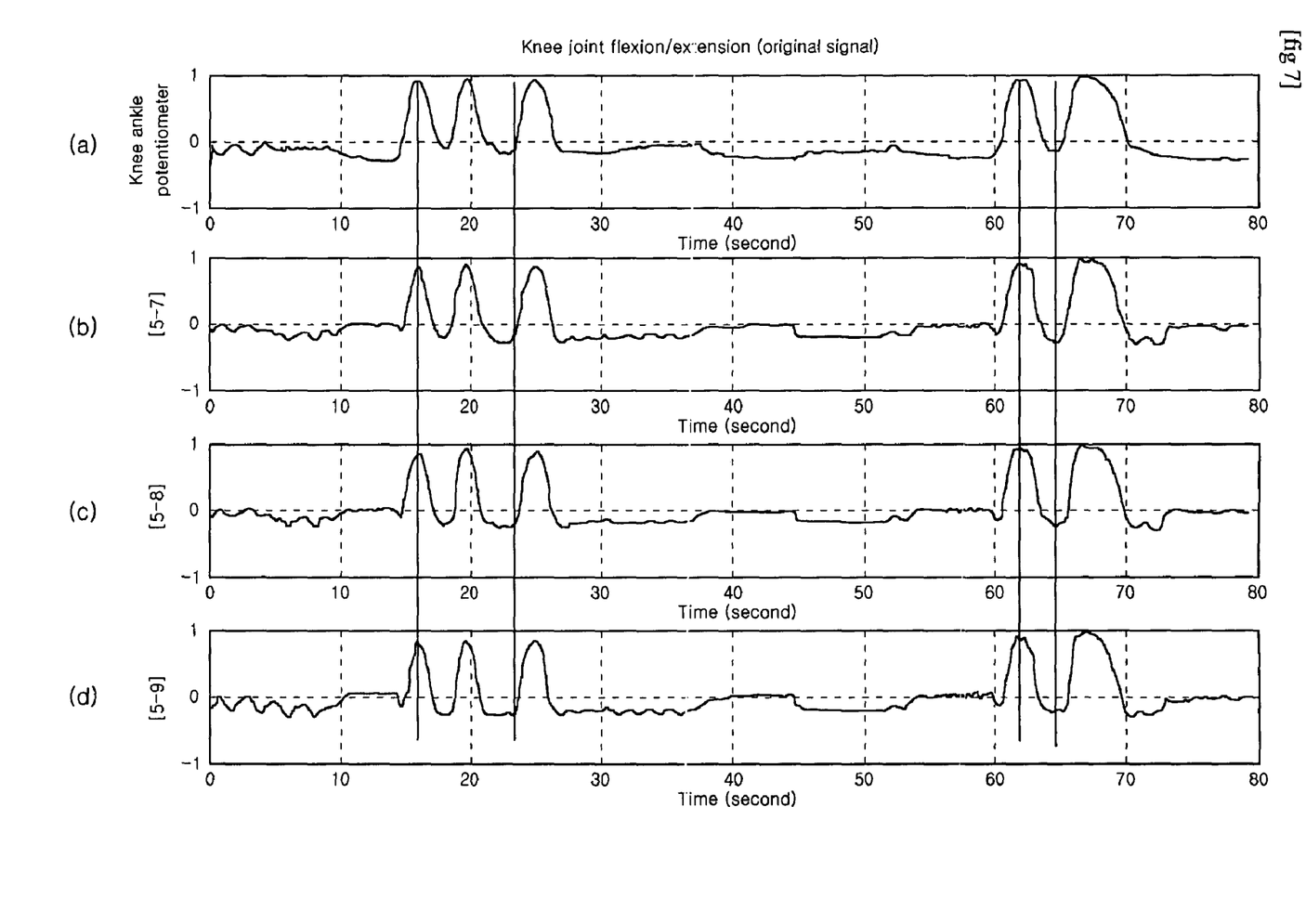
FIGS. 7a to 7d are graphs that are presented to compare a signal measured by the electronic goniometer with signals measured by the voltage detection electrodes with respect to the detection of the angles of knee joint movement.

FIGS. 7a to 7d show the variations of angles during the flexion and extension movements of a knee joint, in which FIG. 7a shows values measured by the electronic goniometer, FIG. 7b shows values measured by a voltage detection electrodes Nos. 5 and 7 pair, FIG. 7c shows values measured by a voltage detection electrodes Nos. 5 and 8 pair, and FIG. 7d shows values measured by a voltage detection electrodes Nos. 5 an 9 pair. The positions of electrode signals having the lowest influence of interference as a result of an analysis of the influence of interference due to joint movement other than knee joint movement and the highest correlation with the signals of the goniometer are selected as optimal electrode positions.

It can be appreciated from FIGS. 7a to 7d that a bio-impedance signal most similar to the values measured by the electronic goniometer is obtained by the voltage detection electrodes Nos. 5 and 7. Accordingly, it can be ascertained from these tests that the optimal positions of voltage detection electrodes capable of accurately detecting knee joint movement are the positions of voltage detection electrodes Nos. 5 and 7 shown in FIG. 2.

FIGS. 8a to 8d are graphs that are presented to compare a signal measured by the electronic goniometer with signals measured by the voltage detection electrodes with respect to the detection of the angles of hip joint movement.

Figure 8:
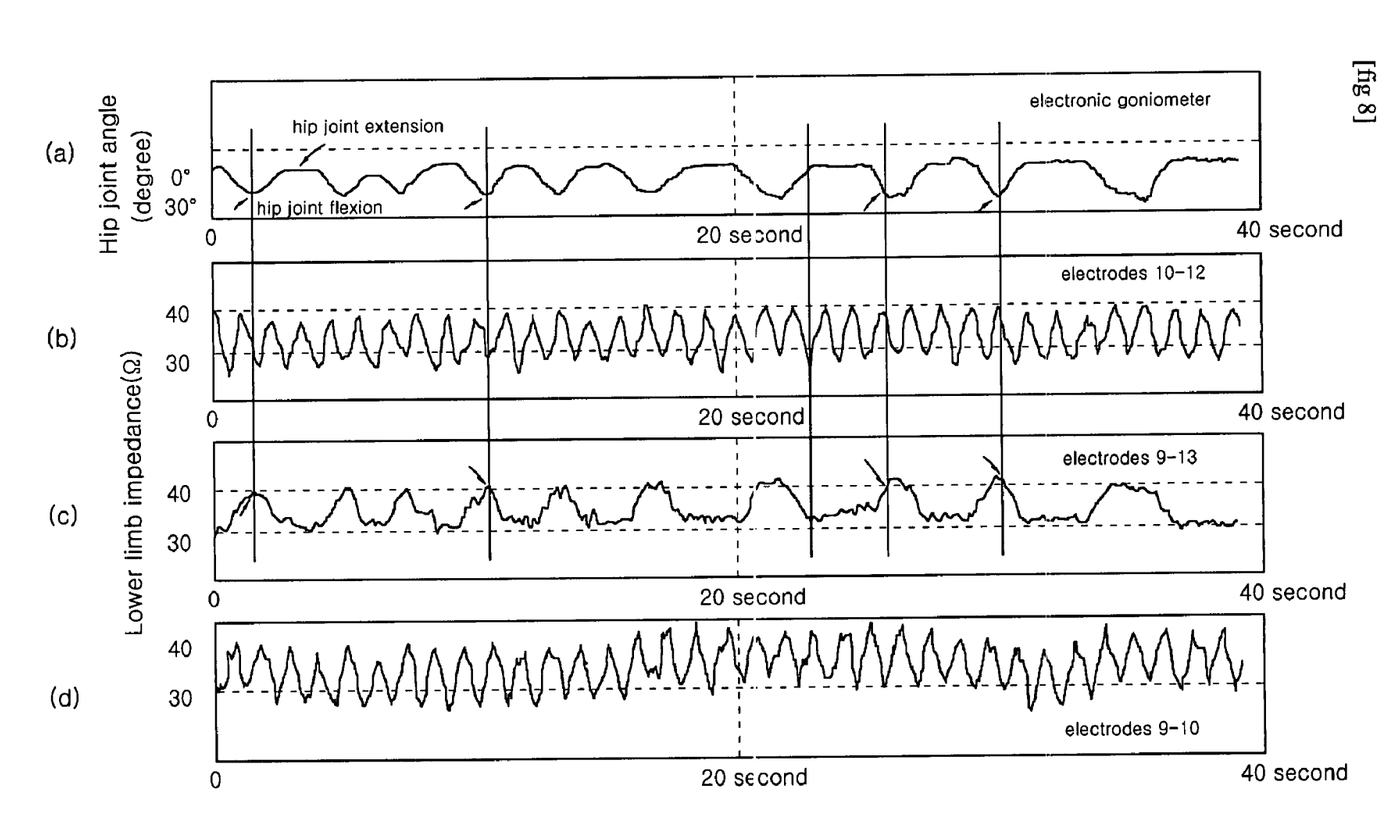
FIGS. 8a to 8d are graphs that are presented to compare a signal measured by the electronic goniometer with signals measured by the voltage detection electrodes with respect to the detection of the angles of hip joint movement.

FIGS. 8a to 8d show the variations of angles during the flexion and extension movements of a hip joint, in which FIG. 8a shows values measured by the electronic goniometer, FIG. 8b shows values measured by a voltage detection electrodes Nos. 10 and 12 pair, FIG. 8c shows values measured by a voltage detection electrodes Nos. 9 and 13 pair, and FIG. 8d shows values measured by a voltage detection electrodes Nos. 9 an 10 pair. It can be appreciated from FIGS. 8a to 8d that a bio-impedance signal most similar to the values measured by the electronic goniometer is obtained by the voltage detection electrodes Nos. 9 and 13. Accordingly, it can be ascertained from these tests that the optimal positions of voltage detection electrodes capable of accurately detecting hip joint movement are the positions of voltage detection electrodes Nos. 9 and 13 shown in FIG. 2.

As described above, the motion of the lower limb can be detected using the bio-impedance signal corresponding to the variation of the motion of the lower limb. It can be ascertained that the flexion and extension movements of an ankle could be detected by use of the impedance variations of gastrocnemius and tibialis anterior, the flexion and extension movements of a knee joint could be detected by use of the impedance variations of musculus quadriceps femoris and musculus biceps femoris, and the flexion and extension movements of a hip joint is principally influenced by semi-membranosus and sartorius. That is, it can be ascertained through comparison with values measured by the goniometer that high correlation exists between the impedance variations and the angular variations of the joints.

Figure 9:
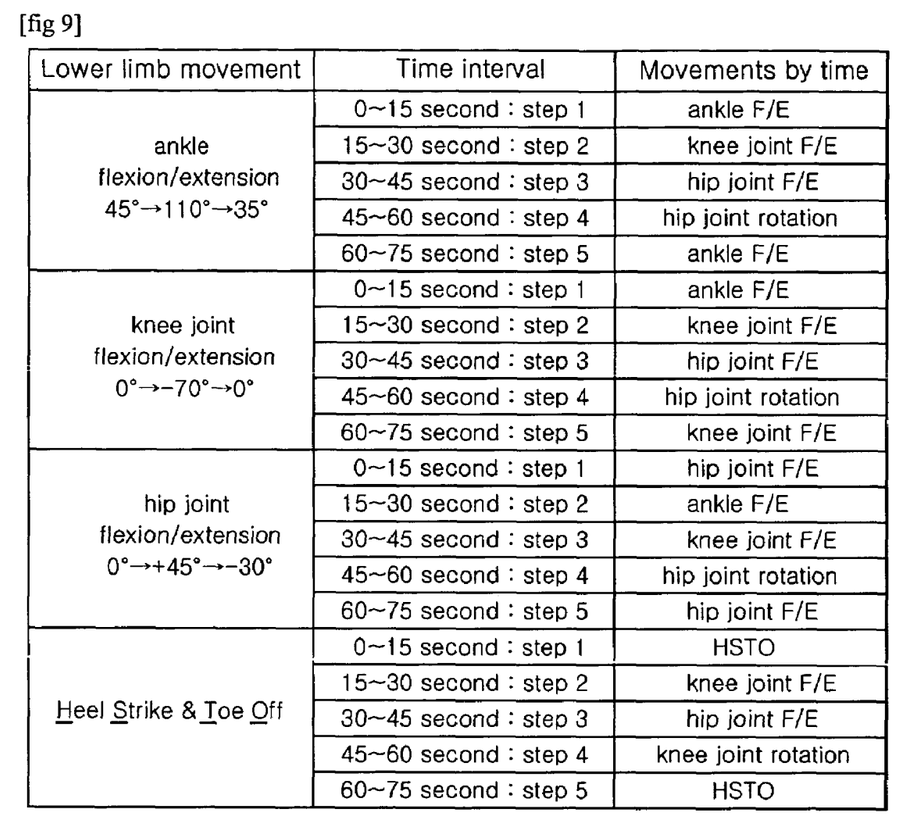
FIG. 9 is a table showing an example of a test method that is used to select an optical voltage detection electrode pair.

FIG. 9 is a table showing an example of a test method that is used to select an optical voltage detection electrode pair. In FIG. 9, the movement of the lower limb includes the flexion and extension movements of an ankle, the flexion and extension movements of a knee joint, the flexion and extension movements of a knee joint, the flexion and extension movements of a hip joint, and the heel-strike and toe-off.

Referring to FIG. 9, in the case of tests on the flexion and extension movements of an ankle, a voltage detection electrode pair attached to the ankle measures the variation of bio-impedance for 75 seconds with the overall time divided into steps at regular intervals of 15 seconds. In more detail, 1) the ankle is flexed and extended for first 15 seconds (that is, 0 to 15 seconds), 2) the ankle is stopped and a knee joint is flexed and extended for next 15 seconds (that is, 15 to 30 seconds), 3) the ankle is stopped and the hip joint is flexed and extended for next 15 seconds (that is 30 to 45 seconds), 4) the ankle is stopped and the hip joint is rotated for next 15 seconds (that is, 45 to 60 seconds), and 5) the ankle is flexed and extended for next 15 seconds (that is, 60 to 75 seconds).

While the movement is performed as described above, signals are extracted from an electronic goniometer and voltage detection electrodes that are attached to the joint. The positions of voltage detection electrodes that detect a signal having the highest correlation with the signal detected by the electronic goniometer are selected as the optimal positions of voltage detection electrodes. The correlation refers to the degree of similarity between values measured by the electronic goniometer and values measured by the voltage detection electrodes.

Figure 10:
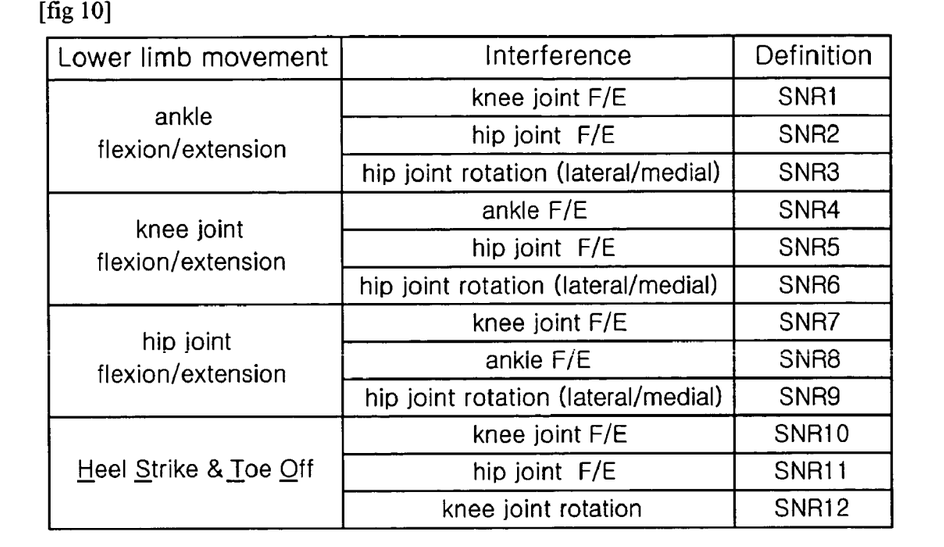
FIG. 10 shows the definitions of Signal-to-Noise Ratios that are used to select an optimal voltage detection electrode pair.

FIG. 10 shows the definitions of Signal-to-Noise Ratios (SNRs) that are used to select an optimal voltage detection electrode pair. These definitions are used to select the optimal positions of voltage detection electrodes, in which interfering signals caused by other joint movement are excluded during each joint movement.

For the flexion and extension movements of the ankle, SNR1 is defined in such a way that an impedance waveform attributable to the flexion and extension movements of the ankle is regarded as a signal and an interference waveform attributable to the flexion and extension movements of the knee joint is regarded as noise, SNR2 is defined in such a way that an impedance waveform attributable to the flexion and extension movements of the ankle is regarded as a signal and an interference waveform attributable to the flexion and extension movements of the hip joint is regarded as noise, and SNR3 is defined in such a way that an impedance waveform attributable to the movement of the ankle is regarded as a signal and an impedance waveform attributable to the rotation of the hip joint is regarded as noise.

For the flexion and extension movements of the knee joint, SNR4 is defined in such a way that an impedance waveform attributable to the flexion and extension movements of the knee joint is regarded as a signal and an impedance waveform attributable to the flexion and extension movements of the ankle is regarded as noise, SNR5 is defined in such a way that an impedance waveform attributable to the flexion and extension movements of the knee joint is regarded as a signal and an impedance waveform attributable to the flexion and extension movements of the hip joint is regarded as noise, and SNR6 is defined in such a way that an impedance waveform attributable to the movement of the knee joint is regarded as a signal and an impedance waveform attributable to the rotation of the hip joint is regarded as noise.

For the flexion and extension movements of the hip joint, SNR7 is defined in such a way that an impedance waveform attributable to the flexion and extension movements of the hip joint is regarded as a signal and an impedance waveform attributable to the flexion and extension movements of the knee joint is regarded as noise, SNR8 is defined in such a way that an impedance waveform attributable to the flexion and extension movements of the hip joint is regarded as a signal and an impedance waveform attributable to the flexion and extension movements of the ankle is regarded as noise, and SNR9 is defined in such a way that an impedance waveform attributable to the movement of the hip joint is regarded as a signal and an impedance waveform attributable to the rotation of the hip joint is regarded as noise.

For the heel-strike and toe-off, SNR10 is defined in such a way that an impedance waveform attributable to the heel-strike and toe-off is regarded as a signal and an impedance waveform attributable to the flexion and extension movements of the knee joint is regarded as noise, SNR11 is defined in such a way that an impedance waveform attributable to the heel-strike and toe-off is regarded as a signal and an impedance waveform attributable to the flexion and extension movements of the hip joint is regarded as noise, and SNR12 is defined in such a way that an impedance waveform attributable to the heel-strike and toe-off is regarded as a signal and an impedance waveform attributable to the rotation of the hip joint is regarded as noise.

A voltage electrode pair that is minimally influenced by an interfering signal, that is, that has the highest SNR, is selected as an optimal voltage detection electrode pair, based on the above-described definitions of SNRs.

Figure 11:
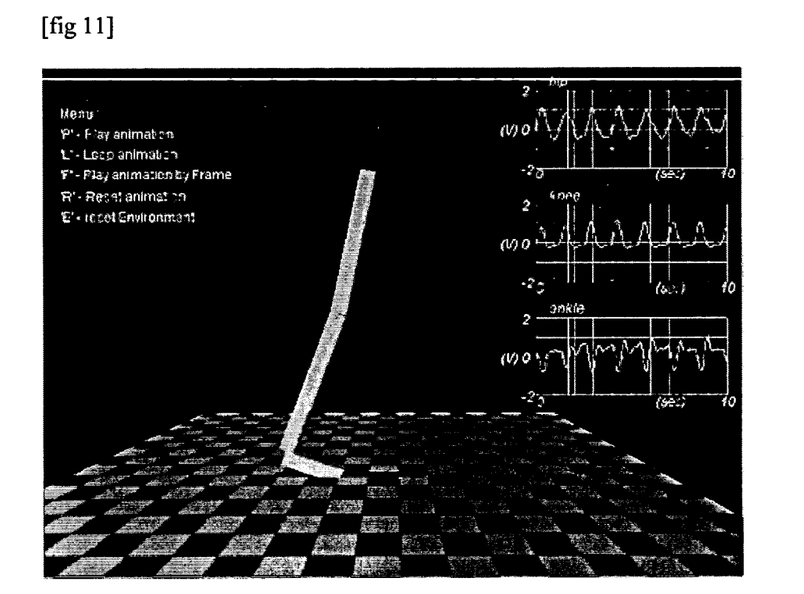
FIG. 11 is a diagram showing an avatar that represents the motion of a lower limb in accordance with an embodiment of the present invention

FIG. 11 is a diagram showing an avatar that represents the motion of the lower limb in accordance with an embodiment of the present invention.

That is, FIG. 11 shows a program for analyzing the motion of a lower limb, which is fabricated so that the angular variations of respective joints according to the motion of the lower limb of an examinee are monitored and analyzed continuously or in stages.

Bio-impedance signals represent the variations of bio-impedance that are detected at the optimal positions of voltage detection electrodes on the regions of a hip joint, a knee joint and an ankle while the examinee makes the motion of the lower limb thereof. These bio-impedance signals are plotted on graphs on the right side of the diagram.

The analysis program is written in WTKTM (version 9) of Sense8 Corporation and Visual $C^{++}$ that are the standardized library of a virtual reality field. In accordance with the above-described analysis program, the motion of the lower limb of the avatar shown in FIG. 11 is controlled to correspond to bio-impedance signals obtained through three channels.

A menu allows a user to select a hot key and execute a desired operation. The user can play continuous animation using a hot key P, can play animation one time using a hot key L, and can analyze the variation of joints at every moment using a hot key F. A hot key R is used to reset animation. The menu is displayed on the right side of FIG. 11, in which "P" denotes Play animation, "L" denotes Loop animation, "F" denotes Play animation by Frame, "R" denotes Reset animation, and "E" denotes Reset environment.

Although specific embodiments have been described in the present specification, various modifications are possible without departing from the scope and spirit of the invention. For example, since the term "living body" includes animals having joints as well as a lower limb and an upper limb, the present invention may be applied to analyses of the motions of the animals.

As described above, in accordance with the present invention, in the case of an analysis of a lower limb, the angular variations of respective joints according to the movement (flexion and extension movement) of an ankle, a knee joint and a hip joint can be detected by use of the variations of bio-impedance. Furthermore, when values measured by the electronic goniometer are compared with values measured by voltage detection electrodes of the present invention, a correlation coefficient r is 0.94 or more, which is considerably high. The correlation coefficient 0.94 is a value that is obtained by cross-correlating a signal detected by the goniometer with a bio-impedance signal detected by the voltage detection electrodes of the present invention.

Furthermore, a high correlation coefficient (−0.97) between the differential values of the variation of bio-impedance of a forearm and the angular velocities of an elbow can be obtained, and the correlation coefficient (0.79) between the variation of bio-impedance of a forearm and the variation of velocity of an arm can be obtained, so there can be proposed a possibility that movement patterns can be observed using the variations of bio-impedance.

The present invention has the following effects.

First, electrodes are attached to the skin of an examinee, so the joint movement of the examinee can be simply detected without the imposition of restriction on the activities of the examinee. The present invention has little spatial limitation, can analyze motions for a long time, and has high time resolution, compared with a conventional mechanical method. The present invention is advantageous in that it has the lower amount of calculation and a higher SNR, compared with a conventional EMG using bio-signals. The present invention can overcome limitations in an analysis of motions, and can accurately detect the motions. The apparatus of the present invention can replace a conventional expensive system for analyzing motions and movement performance.

Second, the development of a relevant science is promoted by the development of a motion analysis and movement analysis system. That is, the present invention contributes to the interpretation of a human body motion mechanism, such as a gait, and systematization and a quantitative analysis can be established by the development of an automatic analysis through the interaction between a hardware system and a computer model and the development of software so as to be applied to clinical uses.

Third, the present invention contributes to the development of an optimal exercise program that is used in the field of sports science. That is, the present invention can be used to improve athletic abilities and athletic postures through the improvement of gait patterns, running postures and athletic actions, and to analyze the performance of movements.

Fourth, the present invention can popularize an efficient motion analysis system capable of replacing a conventional expensive motion analysis system that has been used in the field of rehabilitation medicine. That is, the present invention can be used as a gait analysis system using the measurements of bio-impedance and EMG.

Fifth, the present invention can be used to remotely control a robot that uses only pure bio-signals, and replace a conventional expensive motion capture system that has been used in the fields of virtual reality and animation.

Sixth, in accordance with the present invention, the problems of the conventional technology are overcome by the development of a low cost system capable of obtaining the status information of operations and loads, and the health of the population can be improved by the popularization of motion analysis technology.

Seventh, in accordance with the present invention, it is possible to expand channels so as to variously and minutely analyze the movements of lower limbs, such as a gait analysis. Additionally, if wireless technology is adopted, the present invention can be used in the field of sports that causes many spatial movements and requires long-term continuous measurements, differently from conventional goniometer and video image analyzer capable of perform measurements only in limited space.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of measuring bio-impedance attributable to joint movement, comprising the steps:
    generating a weak current by use of a constant current source;
    causing the weak current to flow from a point to another point;
    forming L voltage detecting electrode pairs from voltage detecting electrodes positioned at m points on each of n-1 lines that divide an interval between a first joint and a second joint, between which the weak current flows, into equal n parts, using a combination equation $_mC_2=L$, where m comprises the number of voltage detecting electrodes, n comprises a total number of lines between a first joint and a second joint, and L comprises the number of voltage detecting electrode pairs;
    detecting bio-impedance at certain periods from J voltage detecting electrode pairs that are obtained by subtracting K voltage detecting electrode pairs, each of which exists on a single dividing line, from the formed L voltage detecting electrode pairs; and
    selecting a pair of voltage detecting electrodes having a highest variation of bio-impedance.

2. The method as set forth in claim 1, wherein the weak current has a frequency of 50 KHz and a magnitude of 300 µA.

3. The method as set forth in claim 1, wherein the m points are two points on each of three lines that equally quadrisect an interval between an ankle and a knee joint between which the weak current flows.

4. The method as set forth in claim 1, wherein the m points are two points on each of three lines that equally quadrisect an interval between an ankle and a knee joint between which the weak current flows, and four points on each of two lines that equally trisect an interval between the knee joint and a hip joint.

5. The method as set forth in claim 1, wherein the m points are four points on each of two lines that equally trisect an interval between the knee joint and a hip joint.

6. The method as set forth in claim 1, wherein the m points are two points on each of three lines that equally quadrisect an interval between an ankle and a knee joint between which the weak current flows, and a certain point between the ankle and toes.

* * * * *